US00PP15166P2

(12) United States Plant Patent
Olesen et al.

(10) Patent No.: US PP15,166 P2
(45) Date of Patent: Sep. 21, 2004

(54) CLEMATIS VITICELLA VARIETY DENOMINATION 'EVIPO023'

(50) Latin Name: *Clematis viticella*
Varietal Denomination: EVIpo023

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 4 days.

(21) Appl. No.: 10/640,795

(22) Filed: Aug. 13, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new Clematis cultivar which is well suited to propagation in glasshouses with a compact growth habit, profuse, light violet blue flowers with a yellow center.

The variety successfully propagates from softwood cuttings and is suitable for cultivation in commercial glasshouses. This new and distinct variety has shown to be uniform and stable in the resulting generations from propagation.

1 Drawing Sheet

Botanical classification: *Clematis viticella.*
Variety denomination: 'EVIpo023'.
Commercial: Early and late flowering cultivar.

SUMMARY OF THE INVENTION/DISCOVERY

The present invention constitutes a new and distinct variety of Clematis which originated from a controlled crossing between Clematis 'Mrs. George Jackman', not-patented, and Clematis 'H. F. Young', non-patented. The two parents were crossed and the resulting seed was planted in a controlled environment. The new variety is named 'EVIpo023'.

'Evipo023' may be distinguished from the seed parent by the following characteristics. Flowers of Clematis 'Mrs. George Jackman' are white with a brown center, while 'Evipo023' is violet blue with a yellow center.

The objective of the hybridization of this Clematis variety for commercial glasshouse and nursery culture was to create a new and distinct variety with unique qualities such as:

1. Light violet blue flowers with a yellow center.
2. Very free flowering, good repeat flowering.
3. Compact habit.
4. Flowers well as a young plant.
5. Suitability for small container use.

These qualities required improvement in Clematis varieties that were in commercial cultivation and the objectives have been substantially achieved in the new variety, as evidenced by the unique combination of characteristics that are present in 'EVIpo023' which distinguish it from all other varieties of which we are aware.

The seeds from the hybridization were germinated and evaluations were conducted of the resulting Clematis plants in a controlled environment.

'EVIpo023' was selected from Raymond J. Evison and Mogens N. Olesen in their Clematis development program in Domarie Vineries Les Sauvagees, St. Sampsons, Guernsey, Channel Islands, United Kingdom in April 1998.

Asexual reproduction of 'EVIpo023' by cuttings was first done by Raymond J. Evison and Mogens N. Olesen in Domarie Vineries Les Sauvagees, St. Sampsons, Guernsey, Channel Islands, United Kingdom in May 1998. This initial and subsequent propagations have demonstrated that the characteristics of 'EVIpo023' are true to type and are transmitted from one generation to the next.

BRIEF DESCRIPTION OF THE DRAWING

The accompanying color illustration show as true as is reasonably possible to obtain in color photographs of this type:

FIG. 1.1 Young stem showing attachment of juvenile leaves with pedicel and closed flower bud;

FIG. 1.2 Mature foliage with petiole;

FIG. 1.3 Flower bud closed, flower bud ¼ open, and juvenile growth;

FIG. 1.4 Open flower, upper side;

FIG. 1.5 Open flower, lower side;

DETAILED DESCRIPTION OF THE VARIETY

The following is a detailed description of 'EVIpo023', as observed in its growth throughout the flowering period in glasshouses at Domarie Vineries Les Sauvagees, St. Sampsons, Guernsey, Channel Islands, United Kingdom. Certain phenotypical characteristics of the variety may vary under different environmental, cultural, agronomic, seasonal, and climatic conditions. Plants were grown in 2 liter pots in an unheated glasshouse for 2 years. Color references are made using The Royal Horticultural Society (London, England) Colour Chart, 2001.

For a comparison, the nearest existing Clematis variety is Clematis 'H. F. Young,' a non-patented variety. Chart 1 details several physical characteristics of 'Evipo023' and 'H. F. Young'.

CHART 1

| | 'EVIpo023' | 'H.F. Young' |
|---|---|---|
| Growth. | Compact: seasons growth normally 1.5 M–2.0 M. | Average: seasons growth normally greater than 2.0 M. |

CHART 1-continued

| | 'EVIpo023' | 'H.F. Young' |
|---|---|---|
| Flowering as a young plant. | Very good. | Average. |
| Flower size. | Medium 90–120 mm diameter | Large 150–180 mm diameter |

Parent information: Pollen parent=Clematis 'Mrs. George Jackman'. Seed parent=Clematis 'H. F. Young'.

FLOWER AND FLOWER BUD

Blooming habit: Spring and Autumn, can be recurrent if pruned accordingly.

Flower bud:

*Size.*—25 mm–35 mm in length. Bud diameter is 12 to 15 mm.

*Bud form.*—Ovoid.

*Bud color.*—RHS 138C of the Green Color Group at ¼ opening. Afterwards Color is RHS 91A of the Violet Blue Color Group.

*Peduncle.*—Surface: Smooth Length: 60 mm–90 mm average length. Color: Medium green. RHS 137C of the Green Group. Strength: Erect.

*Receptacle.*—Surface: None.

*Borne.*—In clusters. Compound Cymes and some early season flowers may be borne singly.

Flower bloom:

*Size.*—Medium 90 mm–120 mm on average. Flower depth is 5 to 10 mm.

*Form.*—Upon opening, flat to concave with tepals normally straight.

*Color.*—Upon opening, the upper surface is RHS 91A of the Violet Blue Color Group. Upon opening the reverse side is RHS 91A of the Violet Blue Color Group with green (RHS 137D) central bar. After opening, the upper surface is RHS 91A of the Violet Blue Group. After opening the reverse surface is RHS 91B of the Violet Blue Color Group. White Group 155B central bar. The base of the tepal is RHS N91C of the Violet Blue Group.

*Variations.*—None.

*Fragrance.*—Very slight.

*Lastingness.*—On plants, flowers last 10 to 20 days.

Tepals:

*Tepal Count.*—Average range: 6–8, Normally 8.

*Shape.*—Individual tepal shape is elliptic.

*Size.*—50 to 60 mm long. 25 to 35 mm wide.

*Cross section.*—Flat.

*Margin.*—Entire.

*Undulation of margin.*—Weak.

*Apex.*—Acute.

*Base.*—Acute.

*Recurvature of tip.*—Occasional tip recurvature.

*Persistence.*—Tepals drop off cleanly.

*Arrangement.*—Tepals are arranged regularly.

Reproductive organs:

*Filaments.*—Medium-long length 8–12 mm. Color: White Group 155A.

*Anthers.*—Medium length 5–8 mm. Color: Yellow Group 2D.

*Pollen.*—Color: Yellow Group 2D.

*Stigmas.*—May protrude slightly from between the anthers (stigma colour=RHS Yellow Group 2D.)

*Pistils.*—50 to 70 in quantity.

PLANT

Plant form: Climbing and spreading.

Plant growth: Compact.

Height: Seasons growth attains 1.5–2.0 meters.

Spread: 0.5 to 1 meter.

Hardiness: Trials to date show the variety is cold tolerant to USDA Hardiness Zones 4–9.

Stems:

*Size.*—Diameter is typically 4 mm. Length from base of plant to flower is 0.8 to 1 meter.

*Color.*—Young wood: Green Group 137C Turning to Greyed Red Group 178B. Older wood: Greyed Red Group RHS 178B. After several seasons turning to a Greyed orange Group 165C.

*Internodes.*—Cylindrical. Length: 80–120 mm.

*Petioles.*—Incidence: Moderate. Size: Average length: Petiolus=60–90 mm. Petiole=15–50 mm. Color: Green RHS 137C. Clasping: By winding leaf petiolus.

*Bark.*—Young wood: Smooth. Older wood: Smooth.

Plant foliage: Deciduous. 3 Ovate leaflets arranged in pinnate form.

*Terminal leaflet size.*—Medium Length 50 mm to 70 mm (l). Breadth 40 mm–60 mm.

*Compound leaf size.*—180 mm (l)×100 mm (w).

Color of mature leaves: Top: Green Group 137C. Bottom: Green Group 137B.

Color of juvenile leaves: Top and Bottom: Green Group 137C.

Plant leaves and leaflets:

*Stipules.*—Absent.

*Petiole.*—Length: 60–90 mm (petiolus). Underneath: Without prickles.

*Leaf Edge.*—Terminal leaflet margin is entire.

*Shape.*—Base of leaflet: Rounded occasionally cordate. Apex of leaflet: Acute.

*Texture.*—Medium thickness. Upper side: Glabrous with Matte surface. Lower side: Ribbed with Matte finish.

Disease resistance: Subject to any disease that normally attacks the species.

We claim:

1. A new and distinct variety of Clematis plant named 'Evipo023', as illustrated and described herein as a distinct and novel clematis variety due to its abundant violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

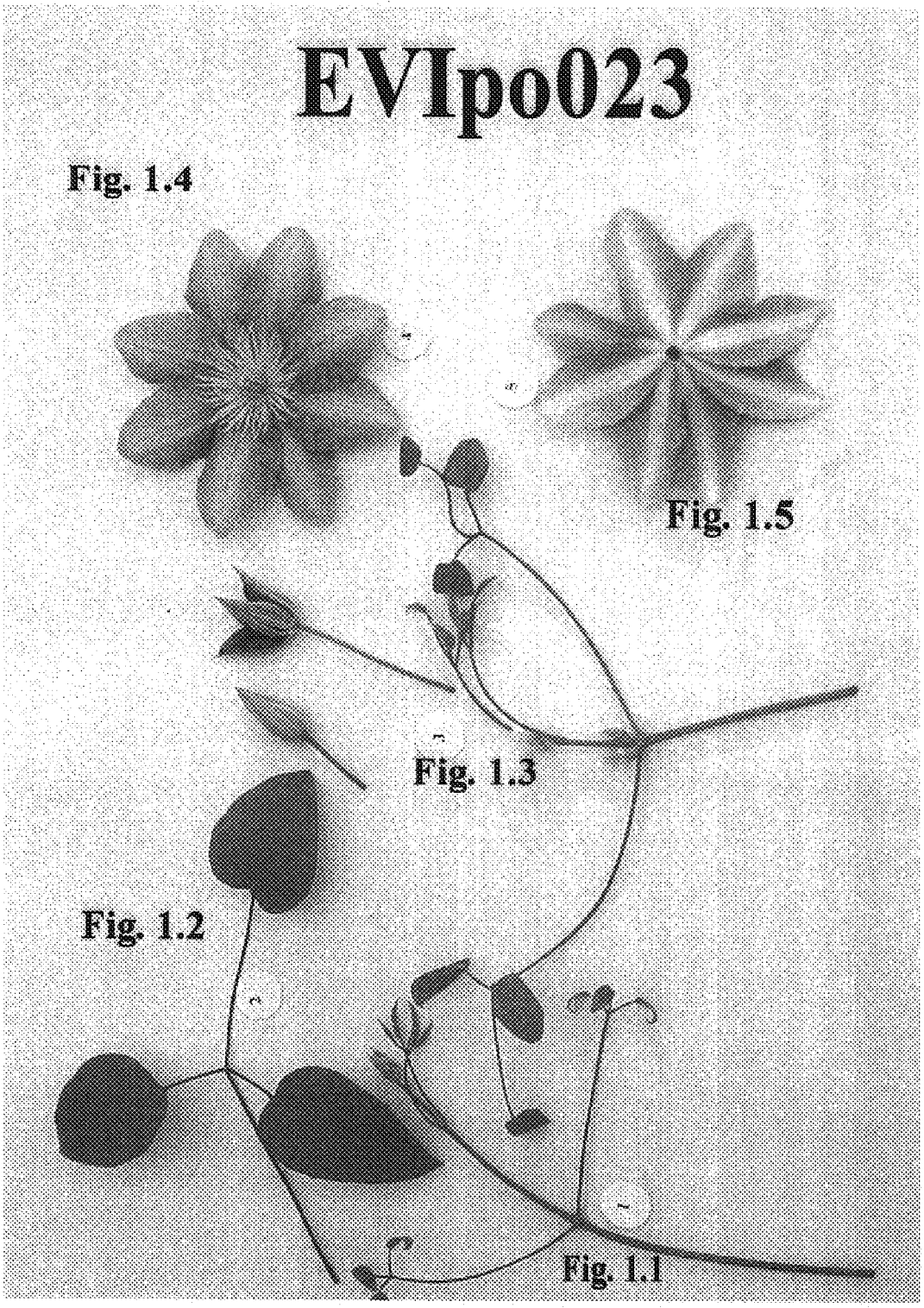
EVIpo023
Fig. 1.4
Fig. 1.5
Fig. 1.3
Fig. 1.2
Fig. 1.1